US011207045B2

United States Patent
Sankaran et al.

(10) Patent No.: US 11,207,045 B2
(45) Date of Patent: *Dec. 28, 2021

(54) SYSTEMS AND METHODS FOR ESTIMATING HEALTHY LUMEN DIAMETER AND STENOSIS QUANTIFICATION IN CORONARY ARTERIES

(71) Applicant: HeartFlow, Inc., Redwood City, CA (US)

(72) Inventors: Sethuraman Sankaran, Redwood City, CA (US); Michiel Schaap, Redwood City, CA (US); Leo Grady, Redwood City, CA (US)

(73) Assignee: HeartFlow, Inc., Redwood City, CA (US)

( * ) Notice: Subject to any disclaimer, the term of this patent is extended or adjusted under 35 U.S.C. 154(b) by 37 days.

This patent is subject to a terminal disclaimer.

(21) Appl. No.: 16/749,560

(22) Filed: Jan. 22, 2020

(65) Prior Publication Data
US 2020/0155106 A1    May 21, 2020

Related U.S. Application Data

(63) Continuation of application No. 15/459,835, filed on Mar. 15, 2017, now Pat. No. 10,575,810.
(Continued)

(51) Int. Cl.
*A61B 6/00* (2006.01)
*A61B 5/02* (2006.01)
(Continued)

(52) U.S. Cl.
CPC ........ *A61B 6/5217* (2013.01); *A61B 5/02007* (2013.01); *A61B 6/032* (2013.01);
(Continued)

(58) Field of Classification Search
None
See application file for complete search history.

(56) References Cited

U.S. PATENT DOCUMENTS 10,575,810 B2 * 3/2020 Sankaran ............... A61B 6/468
2003/0171894 A1 9/2003 Mancini et al.
(Continued)

FOREIGN PATENT DOCUMENTS

JP      2013165874 A    8/2013
JP      2015180292 P    10/2015
(Continued)

OTHER PUBLICATIONS

Van Belle et al. "Value of Percent Coronary Stenosis to Predict Fractional Flow Reserve (FFR) in Patients with Intermediate Coronary Lesions: Insights From A Large French Multicenter Registry". Circulation, vol. 124, No. 21, Nov. 2011, pp. 1-2.
(Continued)

*Primary Examiner* — Edward Park
(74) *Attorney, Agent, or Firm* — Bookoff McAndrews, PLLC

(57) ABSTRACT

Systems and methods are disclosed for predicting healthy lumen radius and calculating a vessel lumen narrowing score. One method of identifying a lumen diameter of a patient's vasculature includes: receiving a data set including one or more lumen segmentations of known healthy vessel segments of a plurality of individuals; extracting one or more lumen features for each of the vessel segments; receiving a lumen segmentation of a patient's vasculature; determining a section of the patient's vasculature; and determining a healthy lumen diameter of the section of the patient's vasculature using the extracted one or more features for each of the known healthy vessel segments of the plurality of individuals.

20 Claims, 7 Drawing Sheets

Related U.S. Application Data

(60) Provisional application No. 62/309,376, filed on Mar. 16, 2016.

(51) Int. Cl.

| | | |
|---|---|---|
| *G06T 7/62* | (2017.01) | |
| *G06T 7/00* | (2017.01) | |
| *G16H 30/40* | (2018.01) | |
| *G16H 50/30* | (2018.01) | |
| *A61B 6/03* | (2006.01) | |
| *G16H 40/67* | (2018.01) | |
| *G16H 50/20* | (2018.01) | |

(52) U.S. Cl.
CPC .............. *A61B 6/468* (2013.01); *A61B 6/504* (2013.01); *A61B 6/507* (2013.01); *G06T 7/0014* (2013.01); *G06T 7/62* (2017.01); *G16H 30/40* (2018.01); *G16H 50/30* (2018.01); *G06T 2207/30048* (2013.01); *G06T 2207/30101* (2013.01); *G16H 40/67* (2018.01); *G16H 50/20* (2018.01)

(56) References Cited

U.S. PATENT DOCUMENTS

| | | | |
|---|---|---|---|
| 2007/0019846 A1* | 1/2007 | Bullitt ................... | G06T 7/0014 382/128 |
| 2010/0021025 A1 | 1/2010 | Hof et al. | |
| 2011/0224542 A1 | 9/2011 | Mittal et al. | |
| 2014/0200867 A1 | 7/2014 | Lavi et al. | |
| 2015/0087972 A1 | 3/2015 | Dumont | |
| 2017/0245821 A1* | 8/2017 | Itu ........................ | A61B 5/7267 |

FOREIGN PATENT DOCUMENTS

| | | | |
|---|---|---|---|
| KR | 2015-0122183 A | 10/2015 | |
| WO | WO 2015153362 A1 | 10/2015 | |

OTHER PUBLICATIONS

J. Dodge Theodore et al.: "Lumen Diameter of Normal Human Coronary Arteries", Circulation, vol. 86, No. 1, Jul. 1, 1992 (Jul. 1, 1992), pp. 232-246.

International Search Report and Written Opinion for corresponding Application No. PCT/US2017/022525, dated Jun. 9, 2017, (14 pages).

Huo, Y. et al.: CT-based Diagnosis of Diffuse Coronary Artery Disease on the Basis of Scaling Power Laws, Radiology, 694-701, vol. 268/3, 2013.

Lesage, D. et al.: A review of 3D vessel lumen segmentation techniques: Models, features and extraction schemes, Medical Image Analysis, 819-845 vol. 13/6 (2009).

Schaap, M. et al.: Standardized evaluation methodology and reference database for evaluating coronary artery centerline extraction algorithms, Medical Image Analysis, 701-714, vol. 13(5) (2009).

Sankaran, S., Grady, L. and Taylor, C.A.: Fast computation of hemodynamic sensitivity to lumen segmentation uncertainty. IEEE Transactions on Medical Imaging, 2562-2571, vol. 34(12), 2015.

Shahzad, R., Kirisli, H., Metz, C., Tang, H., Schaap, M., van Vliet, L., Niessen, W, and van Walsum, T.: Automatic segmentation detection and quantification of coronary artery stenosis on CTA, International Journal of Cardiovascular Imaging, 1847-1859, vol. 29(8), 2013.

Kirisli, H.A. et al.: Standardized evaluation framework for evaluating coronary artery stenosis detection, stenosis quantification and lumen segmentation algorithms in computed tomography angiography, Medical Image Analysis, 859-876, vol. 17(8), 2012.

Min, J. K., et al.: Diagnostic accuracy of fractional flow reserve from anatomic CT angiography, JAMA, 1237-1245, vol. 308(12), 2012.

Breiman, L.: Random forests, Machine learning, 5-32, vol. 45(1), 2001.

Katritsis D et al: "Assessment of the hemodynamic significance of coronary artery stenosis: Theoretical considerations and clinical measurements", Progress in Cardiovascular Diseases, Saunders, Philadelphia, PA, US, vol. 34, No. 1, Jul. 1, 1991 (Jul. 1, 1991), pp. 69-88, XP026324632, ISSN: 0033-0620, DOI: 10.1016/0033-620(91)90020-M [retreived on Jul. 1, 1991].

Rahil et al. "Automatic Segmentation, Detection and Quantification of Coronary Artery Stenoses on CTA." The International Journal Of Cardiovascular Imaging, vol. 29, Aug. 8, 2013, pp. 1847-1859.

\* cited by examiner

SYSTEMS AND METHODS FOR ESTIMATING HEALTHY LUMEN DIAMETER AND STENOSIS QUANTIFICATION IN CORONARY ARTERIES

RELATED APPLICATION(S)

This application is a continuation of and claims the benefit of priority to U.S. application Ser. No. 15/459,835, filed Mar. 15, 2017, which claims priority to U.S. Provisional Application No. 62/309,376 filed Mar. 16, 2016, the entire disclosure of which are hereby incorporated by reference in their entireties.

FIELD OF THE INVENTION

Various embodiments of the present disclosure relate generally to imaging and related methods. More specifically, particular embodiments of the present disclosure relate to systems and methods for predicting healthy lumen radius and calculating a vessel lumen narrowing score.

BACKGROUND

Coronary artery disease (CAD) is one of the leading causes of death. CAD may be characterized by acute events or gradual events. Acute events may include plaque rupture that may demand immediate care. Gradual events may include accumulation of plaque, which may lead to progressive anatomic narrowing resulting in ischemia. One of the most widely used non-invasive clinical metrics for diagnosing patients with symptoms of coronary artery disease is percent stenosis derived from coronary computed tomography angiography (cCTA). Estimation of percent stenosis may involve two steps: (1) the measurement of local diameter and (2) the measurement of a reference health diameter. To measure percent stenosis, cCTA may provide information on the extent of anatomical narrowing in different regions of the coronary artery tree. The extent of anatomical narrowing in regions of the coronary artery tree may be a clinical measure used to decide between performing invasive angiography and pressure measurements or deferment of invasive measurements. In some embodiments, the extent of anatomical narrowing may be estimated categorically (e.g. 0%, 1-30%, 31-49%, 50-69%, 70-100%) in a clinic, or sent to a core lab for analysis. Quantitative computed tomography (QCT) and quantitative coronary angiography (QCA) may include methods where percent stenosis may be estimated as a number between 0 and 100. QCA may involve an invasive procedure evaluated on angiograms, and QCT, evaluated on cCTA's, may be time consuming and generally performed in a core lab. Accordingly, a desire exists to provide a safer and less time-consuming method of determining the extent of anatomical narrowing in regions of a coronary artery tree.

Determining the extent of narrowing entails first discerning a reference vessel diameter, e.g., a healthy lumen diameter. However, the estimation of a reference healthy diameter may be challenging in non-focal disease regions, for instance in diffuse, ostial, and bifurcation lesions. A desire also exists to estimate healthy lumen diameter in non-focal lesions.

The foregoing general description and the following detailed description are exemplary and explanatory only and are not restrictive of the disclosure.

SUMMARY

According to certain aspects of the present disclosure, systems and methods are disclosed for predicting healthy lumen radius and calculating a vessel lumen narrowing score. One method of identifying a lumen diameter of a patient's vasculature includes: receiving a data set including one or more lumen segmentations of known healthy vessel segments of a plurality of individuals; extracting one or more lumen features for each of the vessel segments; receiving a lumen segmentation of a patient's vasculature; determining a section of the patient's vasculature; and determining a healthy lumen diameter of the section of the patient's vasculature using the extracted one or more features for each of the known healthy vessel segments of the plurality of individuals.

In accordance with another embodiment, a system for identifying a lumen diameter of a patient's vasculature comprises: a data storage device storing instructions for identifying image acquisition parameters; and a processor configured for: receiving a data set including one or more lumen segmentations of known healthy vessel segments of a plurality of individuals; extracting one or more lumen features for each of the vessel segments; receiving a lumen segmentation of a patient's vasculature; determining a section of the patient's vasculature; and determining a healthy lumen diameter of the section of the patient's vasculature using the extracted one or more features for each of the known healthy vessel segments of the plurality of individuals.

In accordance with yet another embodiment, a non-transitory computer readable medium for use on a computer system containing computer-executable programming instructions for identifying a lumen diameter of a patient's vasculature is provided. The method includes: receiving a data set including one or more lumen segmentations of known healthy vessel segments of a plurality of individuals; extracting one or more lumen features for each of the vessel segments; receiving a lumen segmentation of a patient's vasculature; determining a section of the patient's vasculature; and determining a healthy lumen diameter of the section of the patient's vasculature using the extracted one or more features for each of the known healthy vessel segments of the plurality of individuals.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1:
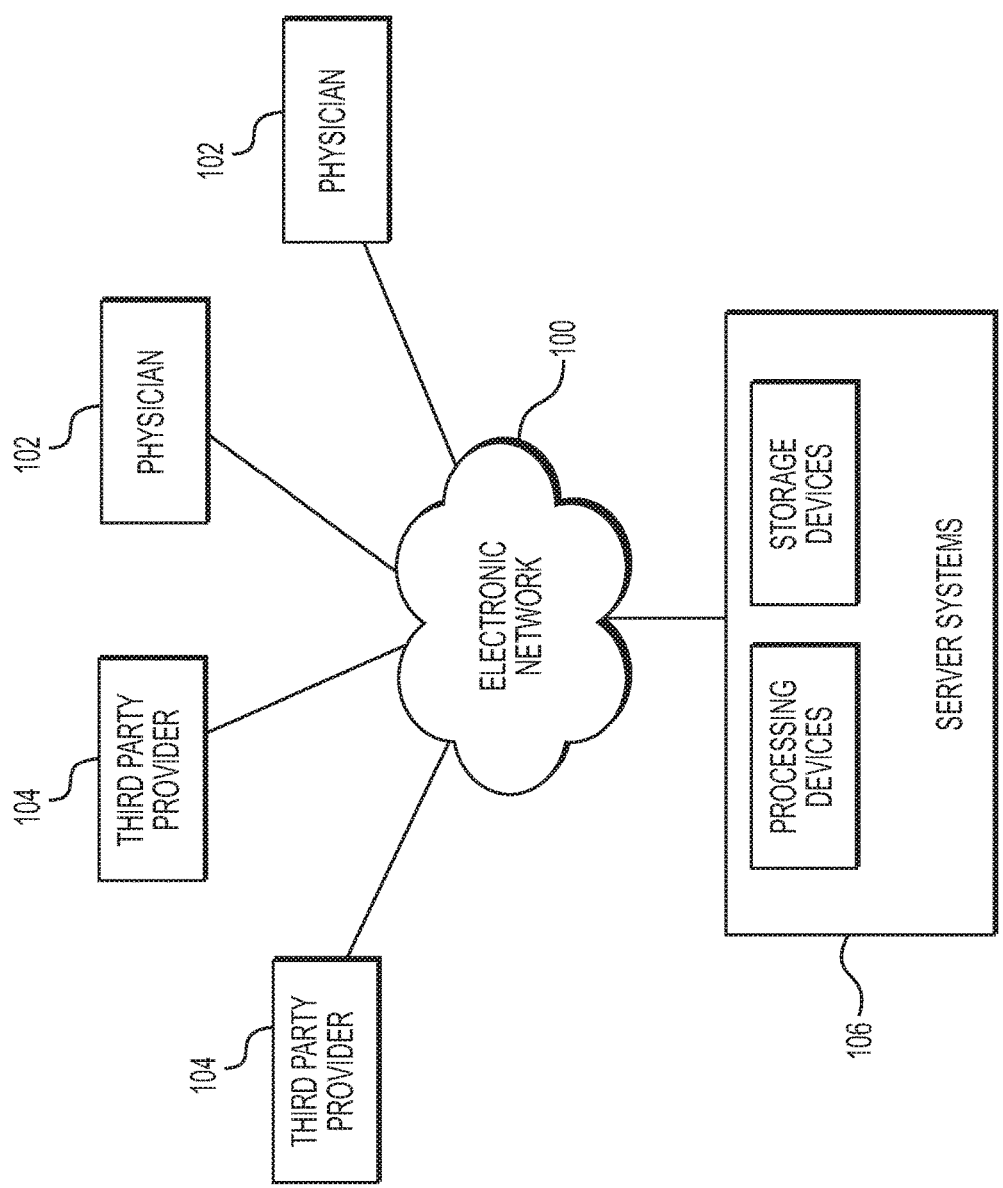
FIG. 1 is a block diagram of an exemplary system and network for predicting healthy lumen radius and calculating a vessel lumen narrowing score (LNS), according to an exemplary embodiment of the present disclosure.

Reference will now be made in detail to the exemplary embodiments of the invention, examples of which are illustrated in the accompanying drawings. Wherever possible, the same reference numbers will be used throughout the drawings to refer to the same or like parts.

While indications of lumen narrowing and percent stenosis are pervasive non-invasive clinical metrics for diagnosing patients with artery disease, current methods involve either quantitative coronary angiography (QCA), evaluated on computed tomography angiography (CTA) data, or quantitative coronary angiograph (QCA), evaluated on angiograms. The QCA methods are invasive and QCT methods are time-consuming and generally performed in core labs or clinics. Accordingly, a desire exists to provide a safer and less time-consuming method of determining the extent of anatomical narrowing in regions of a coronary artery tree.

The present disclosure is directed to noninvasively providing indications of lumen narrowing, percent stenosis, and disease, given a lumen segmentation. Existing efforts often involve determining healthy lumen diameter from finding a patient's vessel lumen diameter upstream of a lesion and a patient's vessel lumen diameter downstream of a lesion. Such methods may capture focal coronary disease, where lesions or stenosis regions may be clearly distinct from normal or healthy vessel lumen. However, such methods may fail to reliably detect lesions where there are no clear indications of healthy (versus diseased) lumen diameters, e.g., in cases of diffuse, ostial, and bifurcation lesions. For diffuse and ostial lesions, for example, areas of disease may span a lengthy portion of a vasculature without presenting apparent narrowings in lumen geometry. In such cases, it may be difficult to discern where a diseased portion of a vasculature may start and end, or what a healthy lumen diameter may be. For bifurcations, even healthy vessels may display a natural reduction in diameter. As a result, healthy lumen diameters are also difficult to determine for vessel bifurcations. Intra-patient estimations/regressions may not be able to estimate reference healthy diameters in these case, due to the absence of clear reference lumen diameter(s).

To estimate a healthy lumen diameter (and thus an indication of lumen narrowing or disease), the present disclosure includes systems and methods that derive healthy lumen diameter(s) with respect to vessel sections derived from sources other than a patient's own vasculature. In one embodiment, the present systems and methods may determine healthy lumen diameter(s) for a patient using a database of healthy vessel sections from individuals, other than vessel sections of the patient. Alternately or in addition, healthy lumen diameters for a patient may be estimated using simulated vessel sections, derived not necessarily from other individuals, but from synthetically generated blood vessels.

The present disclosure is directed to systems and methods for providing an estimate of a geometric lumen narrowing score (LNS), e.g., a ratio of a patient's actual lumen radius to an estimated healthy lumen radius. In an analogous embodiment, the LNS may be based on a ratio of a patient's local vessel diameter to an estimated healthy diameter.

As part of generating an LNS, the present disclosure includes systems and methods for calculating a healthy lumen diameter. In one embodiment, calculating a healthy lumen diameter may be calculated by robust kernel regression or by using a machine learning algorithm. In one embodiment, the robust kernel regression may include multiple regressors, for example, a global kernel fit, a segmental fit, and an anisotropic kernel fit. The different family of regressors may be chosen to encompass different lesion locations (such as ostial, bifurcation), or lesion length (such as focal or diffuse). In one embodiment, the systems and methods may include the selection of one or more regressors to ensure the capture of different lengths and locations of lumen narrowing. Selection of regressors may include several factors, including considerations for minimizing effects of sharp radius variation at vessel branches.

In one embodiment, the machine learning algorithm may determine a healthy lumen diameter with respect to a database of healthy sections from a population of individuals, rather than from intra-patient estimations or regressions. The population-based estimation is shown to predict the diameter of healthy sections more accurately than an intra-patient estimation. Such a method may predict the diameter of healthy sections with a correlation coefficient of 0.95. Compared to anisotropic kernel regression methods, the machine learning method may have a superior area under curve (0.9 vs. 0.83) and a superior operating point sensitivity/specificity (90%/85% vs. 82%/76%) of detection of stenoses. Such a method may also demonstrate superior performance against invasive quantitative coronary angiography, which may be due to superior performance in capturing diffuse, ostial, and bifurcation lesions, and highlighting of difference in sections with non-focal stenoses.

In one embodiment, the present disclosure may include a training phase for training the machine learning algorithm, and a production phase in which the machine learning algorithm may be used to determine healthy lumen diameter (s) for a patient of interest. During the training phase, a machine learning algorithm may learn relationships between upstream and downstream vasculature of given section(s) of vasculature, where the section(s) may include healthy vessel section(s). In other words, the training of such an algorithm may be performed on healthy vessel sections, e.g., from manually annotated healthy and diseased sections. An exemplary machine learning algorithm may use random forest regressors to estimate healthy lumen diameter for a section, using features of vessel segments upstream and downstream of the sections. The machine learning algorithm may include a general framework that may identify regions of lumen narrowing in (coronary) arteries, including focal, diffuse, ostial and bifurcation disease. In one exemplary embodiment, (coronary) arteries may be split into sections or stems, where each stem may be associated with features corresponding to its crown (downstream vasculature), root (upstream vasculature), and/or sibling (the other child vessel of its parent, if available). One embodiment may include predicting the healthy diameter of the stem using a machine learning method trained on these features on a database of stems from a population of individuals. In one embodiment, the machine learning algorithm may further be validated via testing on stems from a second population of individuals. Such machine learning methods may provide an improvement over state-of-the-art techniques, over different lesion characteristics.

During the production phase, machine learning algorithm may determine features of upstream and downstream vasculature of a given section of a patient's vasculature, and map those features to an estimate of a healthy vessel radius. By extension, the present disclosure may be further directed to a production phase of determining a lumen narrowing score for a section of vasculature, with respect to a particular patient. For example, the production phase may include then generating, for a particular patient, a lumen narrowing score mapped to centerlines of the patient's vasculature. In one embodiment, the patient's lumen narrowing score may be validated (e.g., against a manual annotation of lumen segmentation of the patient's vasculature) and/or used to update the machine learning algorithm used to determine the patient's lumen narrowing score.

Healthy lumen diameters and/or LNS may be used in a variety of ways. In one embodiment, a LNS can be used as input to estimate fractional flow reserve (FFR) or sensitivity (e.g., difference in FFR resulting from uncertainty in lumen segmentation). For instance, FFR or sensitivity may be calculated via machine learning algorithms, as described in U.S. application Ser. No. 13/895,893, the entire disclosure of which is incorporated by reference herein. Such algorithms may include multiple features as input to the machine learning algorithms, include geometric features (e.g., minimum upstream diameter, downstream diameter, etc.), anatomical features (lumen diameter, location in the vasculature, etc.), hemodynamic features (blood viscosity, blood pressure, blood flow, etc.), etc. LNS may be included as a feature in the machine learning algorithms for calculating FFR or sensitivity.

Another use of LNS may include using LNS to identify trim plane locations so that location(s) of disease are not trimmed from a model or image. While generating anatomic models, models may be may be trimmed in portions lacking in certainty, e.g., trimming in regions that were not imaged clearly. However, in trimming models, practitioners may want to avoid areas that could be relevant for understanding vascular disease, e.g., sections of narrowing. LNS may help practitioners determine where a model may or may not be trimmed.

Yet another use of healthy lumen diameter or LNS may include using LNS to estimate ideal lumen diameter in terminal vessels. In one embodiment, the estimated ideal/healthy lumen diameter may be used to generate fractal trees, thus simulating vessel structure or vessel morphology past vasculature discernable from image data. Obtaining the fractal trees may then permit the calculation of downstream resistance to blood flow, e.g., by determining healthy vessel area from the healthy lumen diameter and mapping the healthy vessel area to downstream resistance.

Another application of healthy lumen diameter or LNS may include using LNS to estimate regions of disease in vessels so that automated pins may be placed distal to regions with LNS more than a cutoff. In other words, LNS may be used to indicate to a practitioner, areas of lumen narrowing at which the practitioner may initiate a closer study, e.g., by initiating determination of a simulated fractional flow reserve (FFR) value using methods described in U.S. Pat. No. 8,315,812 issued Nov. 20, 2012, to Charles A. Taylor, the entire disclosure of which is incorporated by reference herein. In such a use case, the cutoff may be based on clinician feedback or input, such that sufficient information on lumen narrowing is captured, but a display does not include too many pins.

By extension, LNS may be used to assess locations of disease in a patient's vasculature. For example, the lumen radii from ostia to downstream vasculature may be extracted and a robust kernel regression with a radial basis function may be used to estimate healthy lumen radius. The robust kernel regression approach may further include a modification to account for natural discontinuities in lumen radii in bifurcations that an isotropic kernel may not detect. An exemplary modification to the robust kernel regression may include an anisotropic kernel centered at bifurcations, wherein the anisotropic kernel may be convolved with the Gaussian kernel. Such a modification may provide a robust kernel regression that may more reliably estimate the presence of bifurcation lesions.

Although certain embodiments of the present disclosure are described, for purposes of example, with respect to the diagnosis and treatment of coronary artery disease, the systems and methods described herein are applicable to the prediction of optimal sets of image acquisition parameters in relation to any field of medical imaging.

Referring now to the figures, FIG. 1 depicts a block diagram of an exemplary system and network for predicting healthy lumen radius and calculating a vessel lumen narrowing score (LNS), according to an exemplary embodiment. Specifically, FIG. 1 depicts a plurality of physicians 102 and third party providers 104, any of whom may be connected to an electronic network 100, including the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, including age, medical history, blood pressure, blood viscosity, etc. Physicians 102 and/or third party providers 104 may transmit the anatomical images and/or patient-specific information to server systems 106 over the electronic network 100. Server systems 106 may include storage devices for storing images and data received from physicians 102 and/or third party providers 104. Server systems 106 may also include processing devices for processing images and data stored in the storage devices.

Figure 2A:
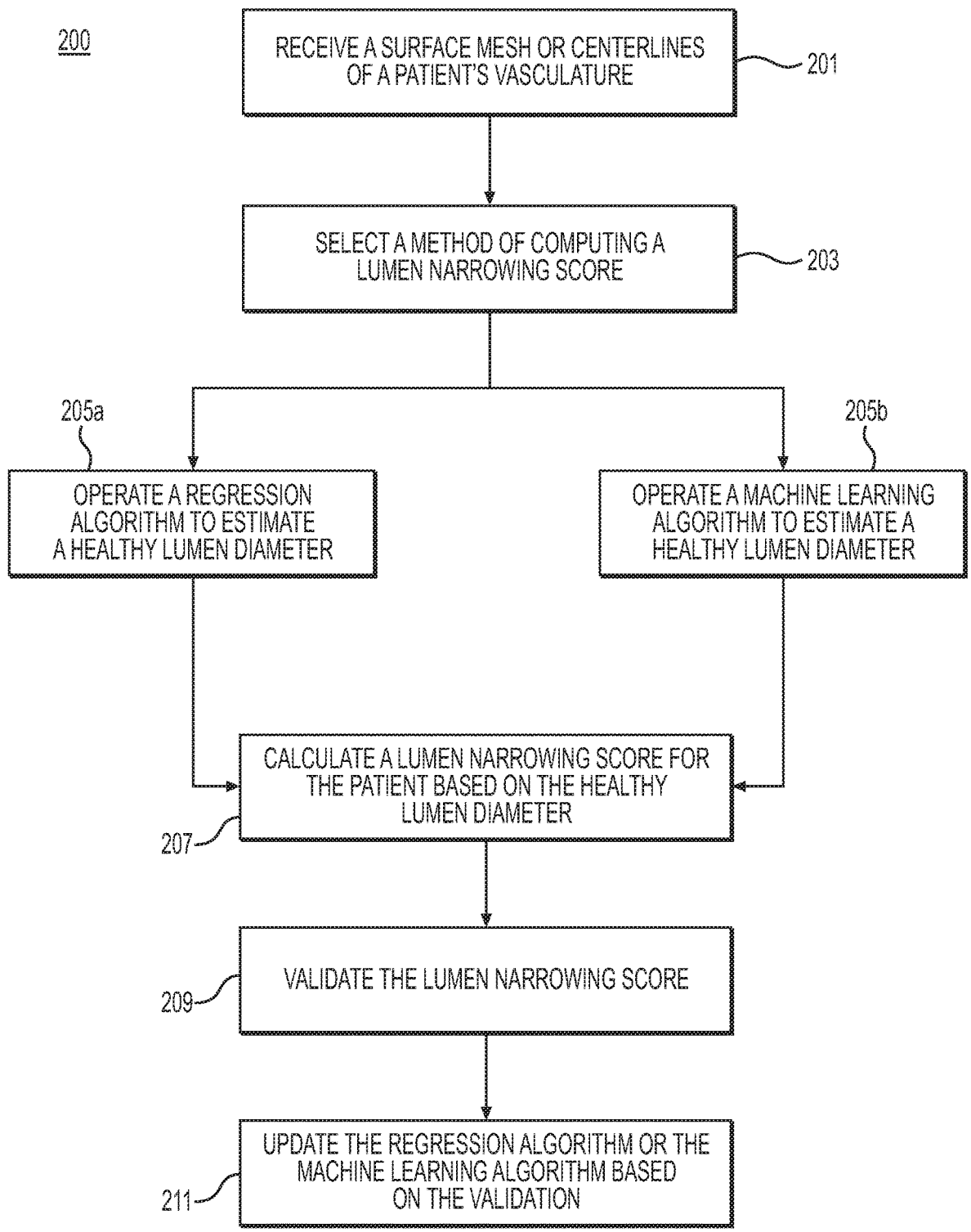
FIG. 2A is a block diagram of an exemplary method of generating estimates of healthy lumen diameter and lumen narrowing scores for a patient, according to an exemplary embodiment of the present disclosure.
Figure 3A:
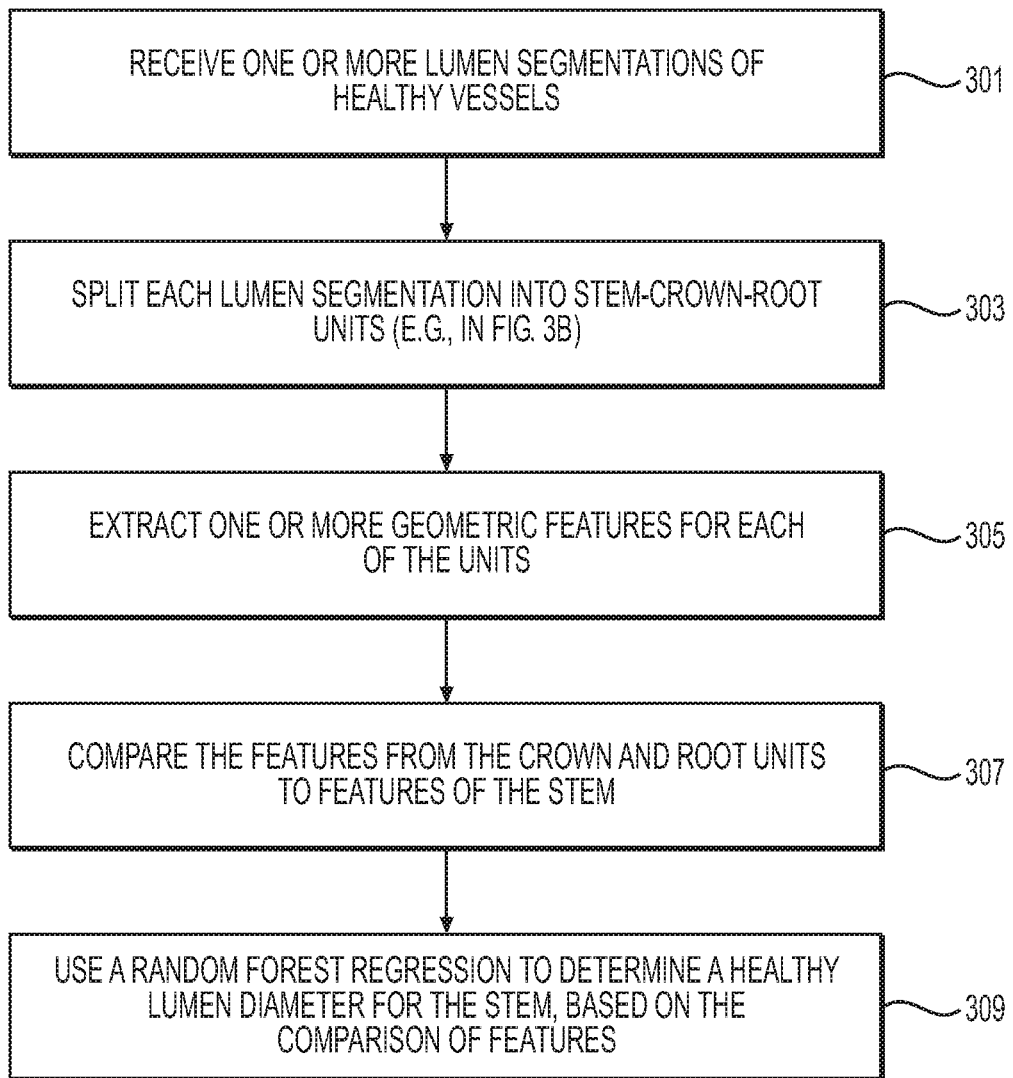
FIG. 3A is a block diagram of an exemplary method 300 of a training phase for developing a machine learning algorithm for generating an estimate of a healthy lumen diameter (which may be used to calculate a lumen narrowing score), according to an exemplary embodiment of the present disclosure.
Figure 3B:
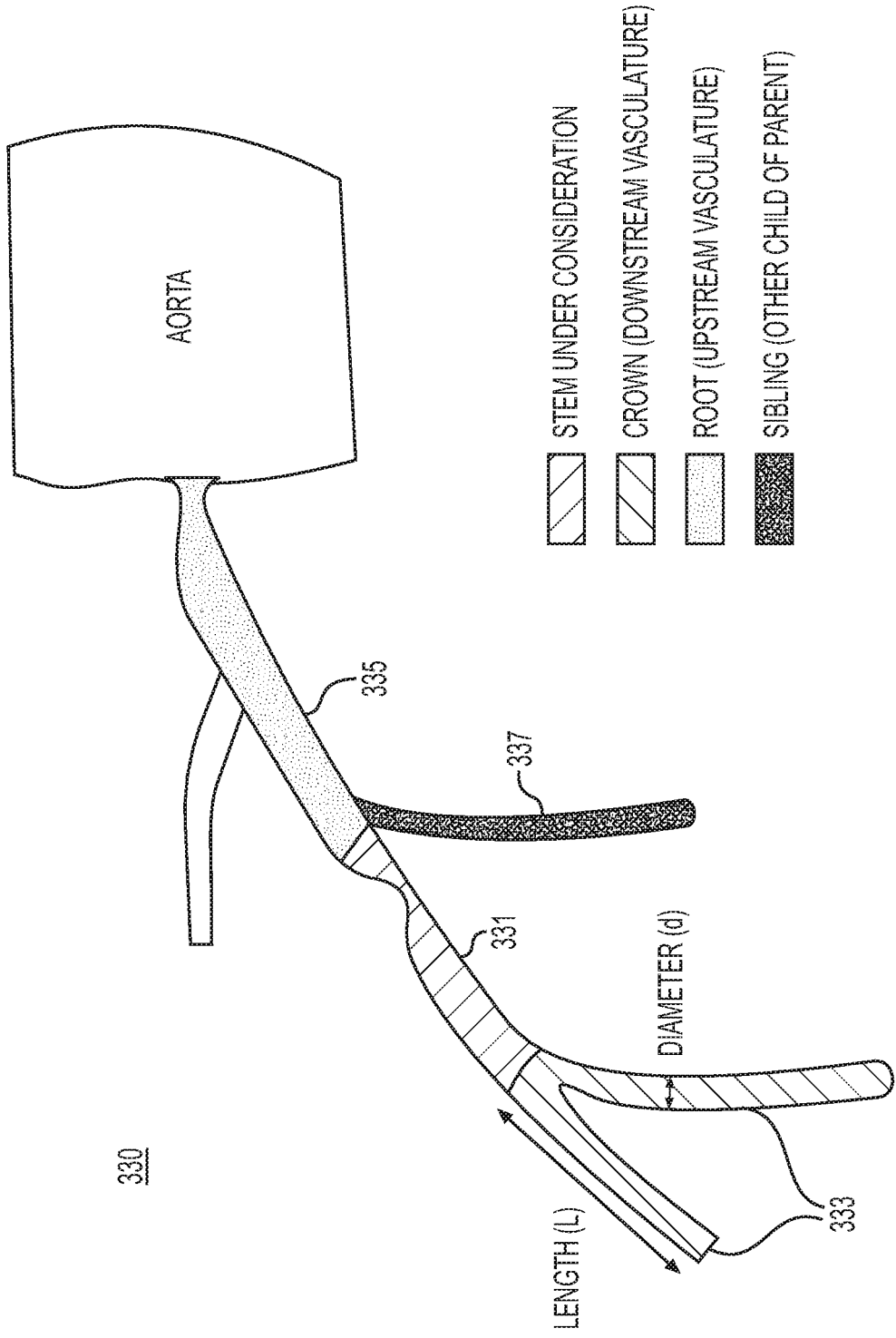
FIG. 3B is an exemplary vascular tree of the machine learning algorithm of FIG. 3A, according to an exemplary embodiment of the present disclosure.
Figure 3C:
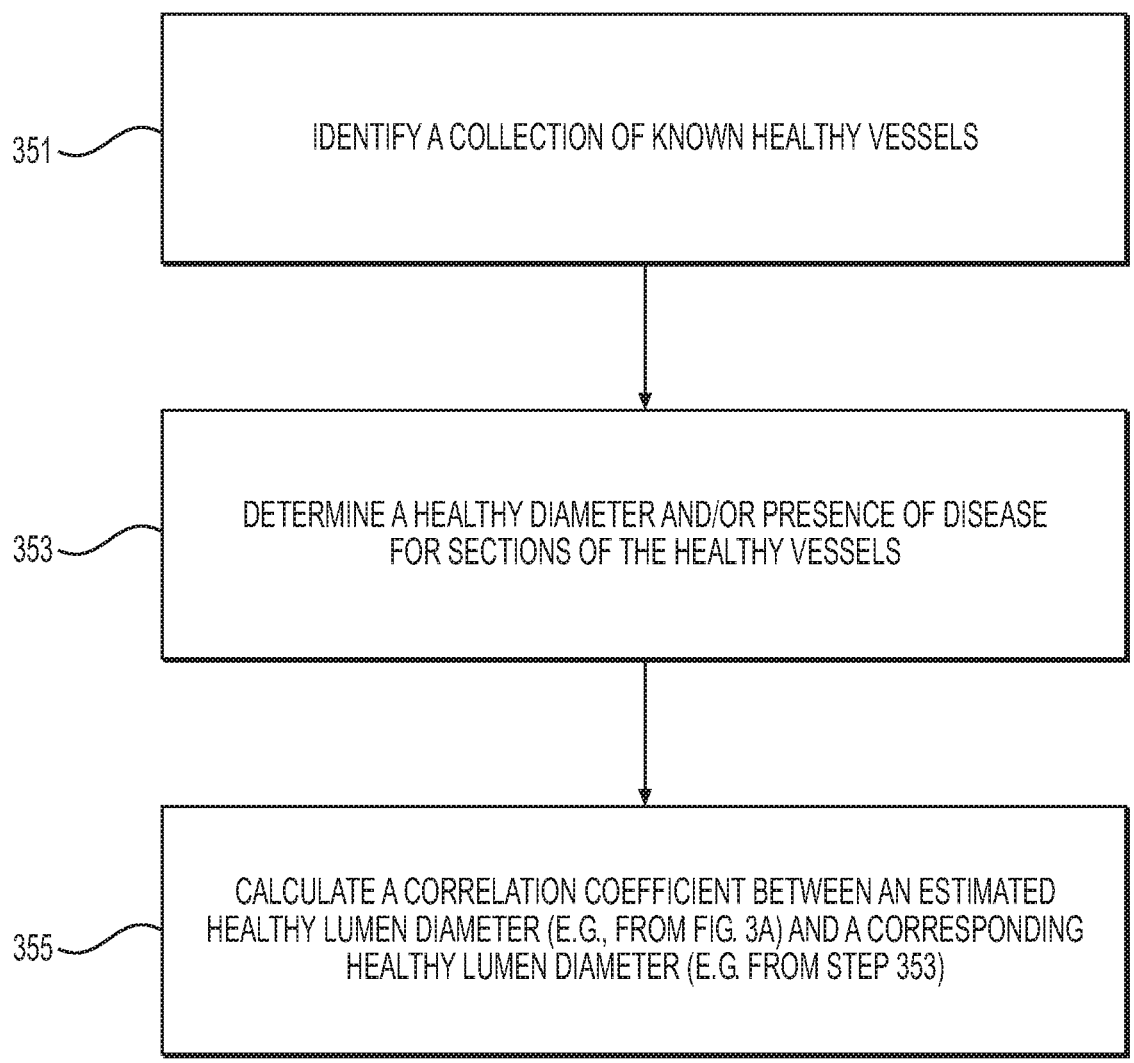
FIG. 3C is a block diagram of an exemplary method of improving or further training a machine learning algorithm for generating a lumen narrowing score by validating the trained machine learning algorithm described in FIG. 3A, according to an exemplary embodiment of the present disclosure.

FIG. 2A is directed to a general embodiment for a method of generating estimate(s) of healthy lumen diameter or lumen narrowing score(s). One way of determining healthy lumen diameter may include a machine learning approach. FIGS. 3A-3C describe training such a machine learning approach, and FIG. 4 describes applying the machine learning approach to estimating healthy lumen diameter or radii for a particular patient.

FIG. 2A is a block diagram of an exemplary method 200 of generating estimates of healthy lumen diameter and lumen narrowing scores for a patient, according to an exemplary embodiment. The method of FIG. 2A may be performed by server systems 106, based on information, images, and data received from physicians 102 and/or third party providers 104 over electronic network 100.

In one embodiment, step 201 may include receiving inputs for algorithms used to generate a healthy lumen diameter or a LNS. For example, step 201 may include receiving anatomical inputs, including a surface mesh or including centerlines of at least a portion of a patient's vasculature. The surface mesh may include a three-dimensional surface mesh. The centerlines may include centered centerlines. In one embodiment, the inputs may include extracting vascular features from a lumen segmentation, e.g., extracting a coronary centerline tree. For example, automatic measurements may be extracted from a lumen segmentation. Any type of lumen segmentation may be used. In one embodiment, trained CT readers may evaluate the lumen segmentation and possibly make corrections. In another embodiment, the inputs may be a vector of radii, along with a corresponding bifurcation indicator (0 or 1 depending on if this point corresponds to a bifurcation), and the parent index for each entry in the vector.

In one embodiment, step 203 may include selecting an algorithm to be used to determine a healthy lumen diameter or a LNS. The algorithms may include a kernel regression algorithm or a machine learning algorithm. In one embodiment, a kernel regression algorithm may be presented as a default. Alternatively, a machine learning algorithm may be set as a default algorithm of determining a LNS. In another embodiment, method 200 may present regression and machine learning algorithms for selection, without a default setting. The selection may be based on input received from a user, default settings in a particular use case or clinic, and/or patient characteristics.

In selecting whether to use a kernel regression algorithm or a machine learning algorithm, considerations may include whether the practitioner is evaluating focal lesions or non-focal lesions. Regression may be sufficient for detecting focal lesions, while machine learning may be superior to regression in identifying non-focal stenosis morphologies, e.g., regions of disease in long diffuse lesions, ostial lesions, or lesions which may be present along an entire section.

In one embodiment, step 205a may include operating a regression algorithm. In one embodiment, the regression algorithm may include a kernel regression algorithm of lumen areas across paths from ostium to downstream or terminal vessels. Stenosed regions may be characterized by a detecting a change in a vessel radius while progressing from an upstream vessel section to a downstream vessel section, where the radius decreases, then increases along the length of the vessel. Diseases regions in a vasculature may entail a sharp and abrupt (acute) or long (diffuse) change in lumen radius, and radii may naturally have a sharp decrease at bifurcations (e.g., dictated by Murray's Law). To account for the various expressions of diseases and stenosed regions, the present systems and methods may include a family of global regressors. Global regressors may be used on an entire vasculature, while local regressors may be used to analyze local portions of vasculature of varying size. Regressions of varying scope may be used to infer multiple indexes, and a LNS may be comprised of the indexes in a way that would provide clinicians with a conservative estimate of LNS.

In one embodiment, step 205a may include operating a kernel regression algorithm with a radial basis function to estimate a healthy lumen radius. Alternately or in addition, step 205a may include operating regression algorithm that may include an anisotropic kernel fit, in which an anisotropic kernel centered at bifurcations may be convolved with a Gaussian kernel. The anisotropic kernel fit may account for natural discontinuities in lumen radii at bifurcations and more reliably estimate the presence of bifurcation lesions than the previously-described kernel regression algorithm.

In one embodiment, step 205a may involve using multiple regressors. For example, one exemplary embodiment of step 205a may use three different regressors: a global kernel fit, a segmental fit, and an anisotropic kernel fit. An exemplary global kernel fit may be defined for each path from a vessel root (e.g., an ostium) to leaves, where healthy radius may be given by, $$r_{healthy}^{global}(x) = \frac{\sum_{x'=1}^{n} N(x' \mid x, \sigma_x) w_{x'} r_{x'}}{\sum_{x'=1}^{n} N(x' \mid x, \sigma_x) w_{x'}}$$

An exemplary segmental fit may be defined for each segment between branches, where the healthy radius may be given by, $$r_{healthy}^{segmental}(x) = \frac{\sum_{x'=1}^{n} N(x' \mid x, \sigma_x) I(x', x) w_{x'} r_{x'}}{\sum_{x'=1}^{n} N(x' \mid x, \sigma_x) I(x', x) w_{x'}}$$

An exemplary anisotropic kernel fit may be defined for each path from a vessel root to the leaves, but weighted with a sigmoidal function centered at the nearest ostium designed to minimize the effect of sharp radius variation at the branch, e.g., $$r_{healthy}^{aniso}(x) = \frac{\sum_{x'=1}^{n} N(x' \mid x, \sigma_x) S(x', x) w_{x'} r_{x'}}{\sum_{x'=1}^{n} N(x' \mid x, \sigma_x) S(x', x) w_{x'}}$$

Where the sigmoidal function, S, may be given by $$S(x', x) = \frac{1}{1 + \alpha e^{-k d_o(x', x)}}$$

and $$d_o(x', x) = d(x', x_o) - d(x, x_o) - d(x, x_{up})$$

Once the global healthy radius $r^*_{healthy}(x)$ is calculated, the corresponding index, $$\kappa(x) = \frac{r(x)}{r^*_{healthy}(x)}$$

may be calculated, and a lumen narrowing score ($\lambda$) may be defined as $\lambda(x)=1-\kappa(x)$, if $\kappa<=1$, $\lambda(x)=0$ otherwise.

In one embodiment, five parameters for $\sigma_x$, $\sigma_{max}$, and $r_{x,max}$ may be chosen for each of the regressors, for a total of 15 regressors. Exemplary parameter values for each of the regressors may include the following values, where n may range from 1 to 15.

$\sigma_x = 5.0*(1+(n-3)*0.4)$ $\sigma_{max} = 200.0*(1+(n-3)*0.4)$ $\sigma_r = 0.25*(1+(n-3)*0.4)$ $k = 0.1 + n*0.3$ The different regressors may provide different lengths and locations of lumen narrowing.

In one embodiment, step 205b may include selecting and operating a machine learning algorithm to determine a healthy lumen diameter or a LNS. In one embodiment, the machine learning algorithm may use information of vasculature other than the patient's vasculature to determine healthy diameter. The machine learning algorithm is described in further detail at FIG. 3A.

In one embodiment, step 207 may include calculating a lumen narrowing score. A lumen narrowing score may be calculated from a ratio of an actual radius against a healthy radius, e.g., $$\kappa(x) = \frac{r(x)}{r_{healthy}(x)}$$

where $r_{healthy}(x)$ may include the theoretical healthy radius of the lumen (e.g., provided by a kernel regression algorithm or a machine learning algorithm), and r(x) may include a radius of a maximum inscribed sphere within a lumen. A maximum inscribed sphere within a lumen may be determined by finding the closest point from a vessel centerline to the surface of a the mesh.

In one embodiment, step 209 may include validating the calculated lumen narrowing score. For example, a LNS may be validated via direct clinical data that outputs lumen narrowing at spatial resolution of centerlines, or an automated vessel labeling tool that may provide a comparison of overall lumen narrowing in major vessels (pLAD, dLAD), etc. Lumen narrowing scores calculated from a machine learning algorithm may be validated against scores calculated from manual annotations.

Several processes may exist for manual annotation of sections of disease. For example, trained readers of cCTA may assess lumen segmentation of a cohort of patients and identify locations of lumen narrowing (e.g., percent stenosis >=50%). This process may mimic the process of reading percent stenosis from CT scans in the clinic, e.g., estimated stenoses visually rather than assessing a reference diameter and evaluating the ratio of minimum lumen diameter to the reference diameter. One way to provide confidence in readings may include a scenario where each patient vasculature being assessed by three readers, where only sections that have a consensus read may be used for training and testing. For convenience, the coronary trees may be split into sections, where each section may be marked either "diseased" or "healthy." Sections may be split using locations of bifurcations as separators. Since manual annotation of diseased sections may be performed on the lumen segmentation rather than the cCTA, performance may not depend on the algorithm used for centerline detection and lumen segmentation. Various centerline detection and lumen segmentation methods may be used while validating a lumen narrowing score calculated from a machine learning algorithm, using a manual annotation. Step 211 may include updating the kernel regression algorithm or machine learning algorithm, based on results of the validation.

Figure 2B:
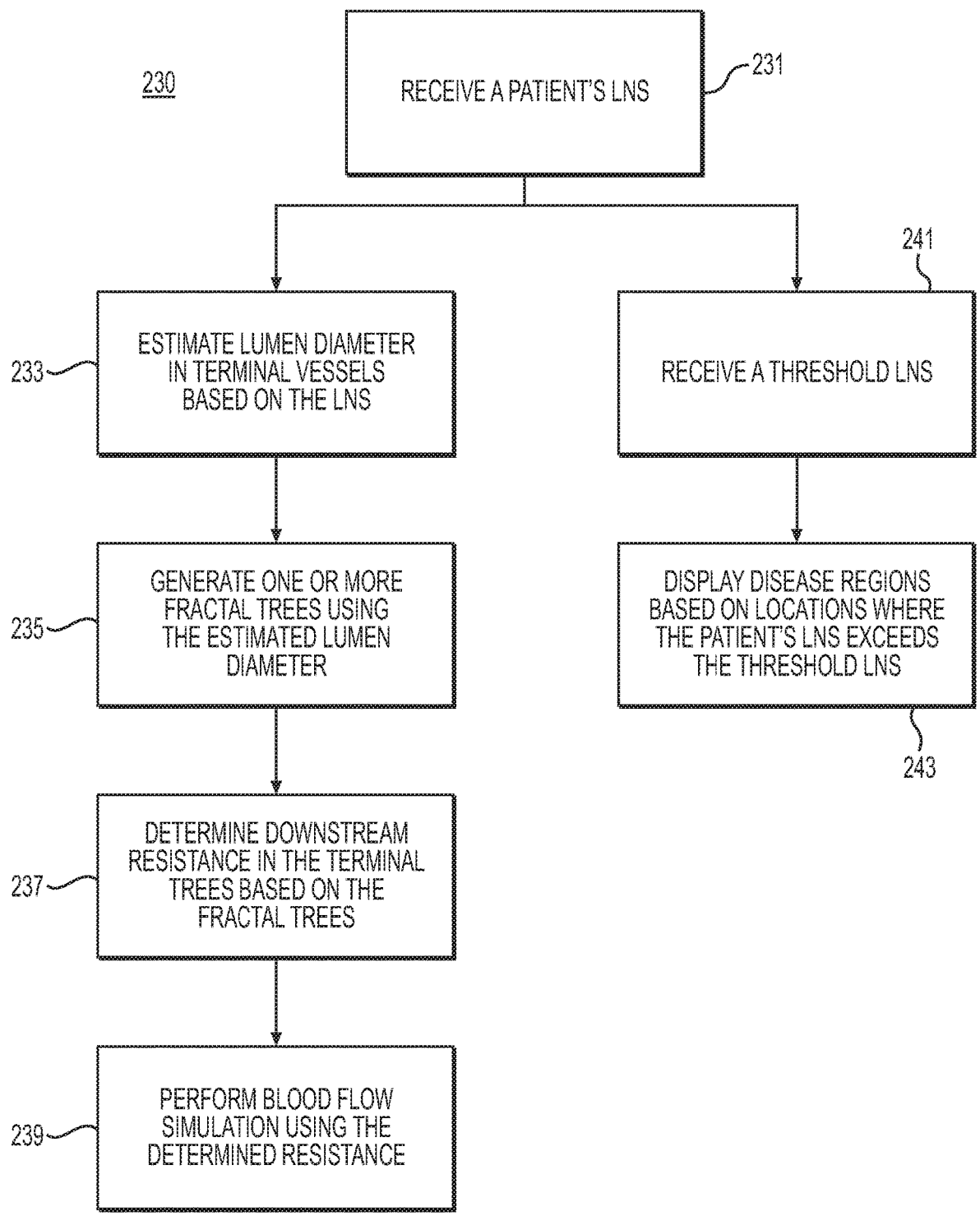
FIG. 2B is a block diagram of an exemplary method of using a LNS to assess a patient's vasculature, according to an exemplary embodiment of the present disclosure.

FIG. 2B is a block diagram of an exemplary method 230 of using a LNS to assess a patient's vasculature, according to an exemplary embodiment. The method of FIG. 2B may be performed by server systems 106, based on information, images, and data received from physicians 102 and/or third party providers 104 over electronic network 100. While the embodiment of method 230 describes exemplary uses of LNS, all of the steps of method 220 may be performed using the healthy lumen diameter or healthy lumen radius, rather than using the LNS.

In one embodiment, step 231 may include receiving a LNS. Steps 233-237 may include using either the LNS to determine resistances of terminal vessels. For example, step 233 may include estimating ideal lumen diameter in a patient's terminal vessels. Step 235 may include generating fractal trees from the estimates of ideal lumen diameter and exemplary step 237 may include determining downstream resistance to blood flow in patient's terminal vessels, based on the fractal trees. The resistance may be used to simulate blood flow through the terminal vessels (e.g., step 239).

In one embodiment, steps 241 and 243 may include exemplary uses for estimating and displaying regions of disease. For example, step 241 may include receiving a threshold LNS, e.g., a threshold which may indicate a location of disease. Step 243 may include generating a display including visual indicator(s) in vessel regions distal to regions with LNS exceeding the threshold LNS. As previously discussed, the threshold LNS may be dictated by clinicians or determined based on clinician feedback such that a sufficient number of disease regions are indicated for a clinician to be able to conduct an analysis, but there are not so many disease regions shown that the analysis is difficult.

Figure 4:
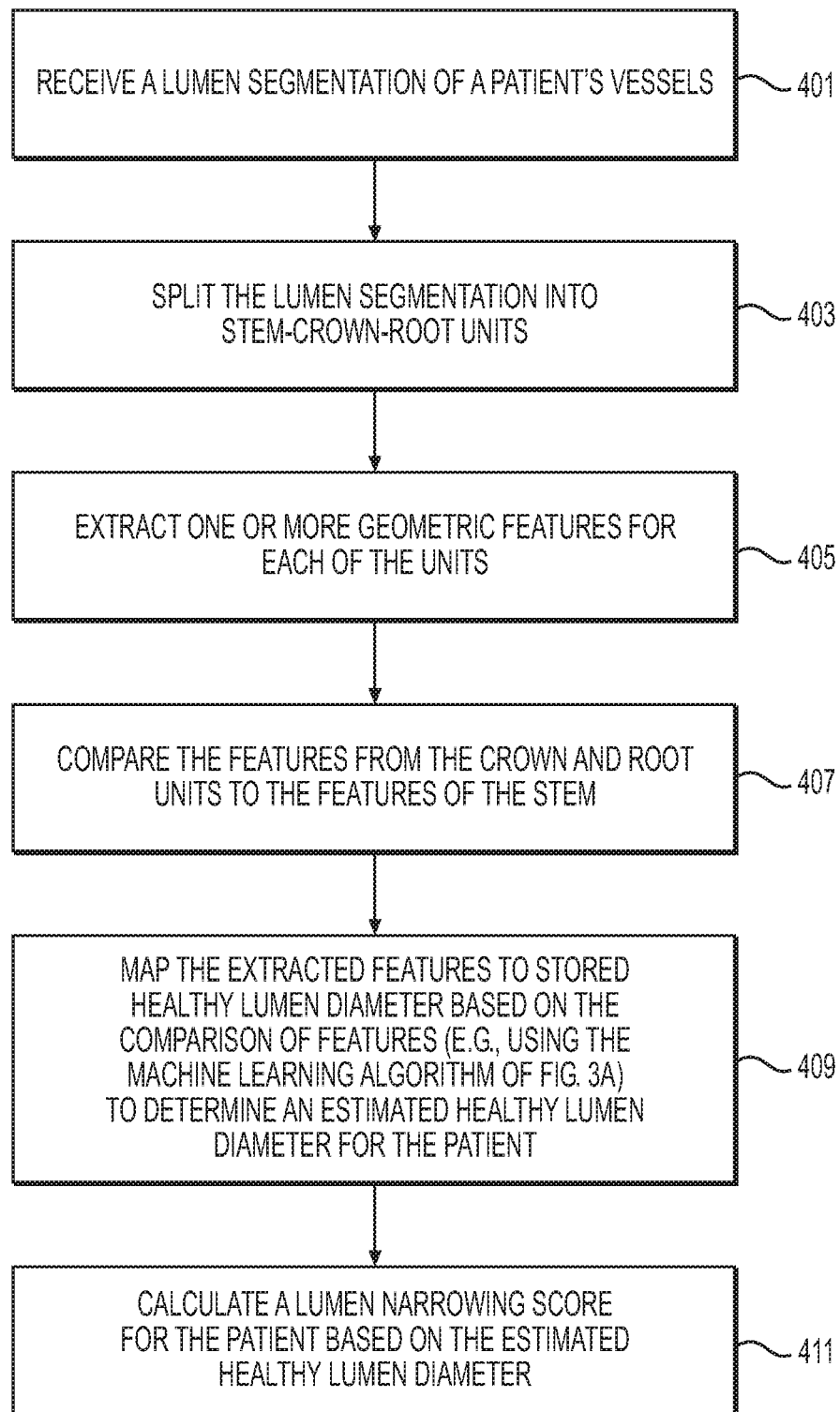
FIG. 4 is a block diagram of an exemplary method 400 of generating a lumen narrowing score for a particular patient, using a machine learning algorithm (e.g., as described in FIG. 3A), according to an exemplary embodiment of the present disclosure.

FIGS. 3A-3C may describe training a machine learning approach. For example, FIG. 3A may include a method for training a machine learning algorithm to conduct a data-driven estimation of a healthy lumen geometry, including defining features of healthy lumen diameter or radii. FIG. 3B may include a diagram for how the machine learning algorithm may analyze sections of vasculature to learn features of healthy vessels. FIG. 3C may include a method for validating the trained machine learning algorithm. FIG. 4 may include calculating an estimate of healthy lumen diameter or radii for a particular patient.

FIG. 3A is a block diagram of an exemplary method 300 of a training phase for developing a machine learning algorithm for generating an estimate of a healthy lumen diameter (which may be used to calculate a lumen narrowing score), according to an exemplary embodiment. Method 300 may include training a machine learning algorithm on a database of healthy sections (e.g., a collection of healthy vessel stems derived from a population of individuals) so that data for a specific patient may be mapped to population-based healthy lumen diameter. The vasculature may include epicardial vasculature. Method 300 may also include testing or validating the machine learning algorithm with test vessel sections from a second population of individuals (as described in more detail in FIG. 3C). While exemplary method 300 describes an embodiment where the training data set includes healthy vessel stems from imaged anatomy of individuals, alternate methods may use synthetic vessel stems. The method of FIG. 3A may be performed by server systems 106, based on information, images, and data received from physicians 102 and/or third party providers 104 over electronic network 100.

Method 300 may further include an exemplary evaluation LNS, as well as any metrics that may be used for validation of the estimation of healthy lumen geometry. Furthermore, LNS may provide indications of a region of disease, for instance, by dividing the local diameter with the estimated healthy diameter, and comparing the quotient to a diagnostic threshold of 50%. In one embodiment, recommendations for treatment may be provided based on the LNS. As an example, exercise medical therapy or exercise may be recommended if LNS less than a cutoff, whereas further invasive tests/procedures may be recommended if LNS is not less than a cutoff.

In one embodiment, step 301 may include receiving lumen segmentations of healthy vessel diameters. For example, step 301 may include receiving annotated lumen segmentations. The annotations may be provided by trained readers (e.g., of cCTA or CT scans) that may assess lumen segmentations for each individual in a plurality of individuals, and identify locations of lumen narrowing (e.g., percent stenosis >–50%). Each lumen segmentation for each individual may be assessed by multiple readers, and sections used to training and testing may include sections that have reads agreed upon by multiple readers. Alternately, annotations may be performed on cCTA data, rather than lumen segmentations. In such an embodiment, centerline detection or lumen segmentation algorithms may affect the training of the machine learning algorithm for determining a healthy lumen diameter (and LNS).

In one embodiment, step 303 may include splitting the each lumen segmentation into stem-crown-root units (e.g., as shown in FIG. 3B). A stem may include a section of interest for which a healthy diameter may be evaluated. A crown may include the vasculature downstream of the section of interest, and a root may include vasculature upstream of the section of interest. The machine-learning method may also include identifying a sibling vessel, which may include a child vessel of the parent vessel, other than the vessel in which the section of interest is located.

In one embodiment, step 305 may include defining and/or extracting features for a vessel segment, e.g., where each segment may represent coronary segmentation between bifurcations. For each stem in a given vasculature, step 303 may include extracting one or more of the following features for the corresponding crown, root, and sibling vessels (when available), e.g., average, maximum and minimum lumen area (A), volume (V), length (L), V/A, and V/L. In one embodiment, features of the machine learning algorithm may include evaluating local diameter using maximum inscribed spheres. An alternative or additional approach may include evaluating planar area, e.g., the area of lumen along the normal to centerlines. Some features may not be available for some stems (e.g., ostial sections may not have a root unit and terminal sections may not have a crown unit). In the machine learning method, such features may be assigned a default special value of –1. In one embodiment, features may be defined for a given section, in which each section may represent coronary segmentation between bifurcations. Since the flow rate in a given section may be constant (or a section may be defined such that flow rate is constant within the section), an exemplary step 305 may assume that a healthy vessel may maintain its radius within a section to preserve a homeostatic state of wall shear stress.

In one embodiment, step 307 may include comparing features from other parts of the vascular tree to the stem under consideration. For example, the machine learning algorithm may analyze one stem at a time and use features from the rest of the vascular tree to infer healthy lumen diameter at the stem under consideration.

In one embodiment, step 309 may include inferring a healthy lumen diameter for a vessel segment. For example, the machine learning algorithm may include using a random forest regression to predict a healthy lumen diameter. Random forests may be effective and powerful for high dimensional and heterogeneous features. Random forests may employ an ensemble of decision trees, each of which may be composed of a random subset of features and training data. Each decision tree may map the input feature vector to a continuous variable. Values from the decision trees may be pooled together and averaged to compute a final predictor of healthy lumen diameter ($d_p$). In one embodiment, multiple random forests may be generated (e.g., one for non-terminal vessels and one for ostial segments). Once a healthy lumen diameter is determined, LNS may be evaluated from the ratio of a local lumen diameter ($d_l$) to the predicted healthy lumen diameter as, $\alpha=(1-d_p/d_l)\times 100\%$. One exemplary scenario may include 50 trees with an average of 5 features per tree. A 5-fold cross validation may be used to evaluate the performance of the chosen parameters.

In one embodiment, subsequent steps may include assessing or validating the machine learning algorithm. For example, the machine learning algorithm may be updated based on the assessment/validation. For instance, assessing/validating the machine learning algorithm may include evaluating the random forest regressor (e.g., of step 309) against manual annotations. In one case, results of the random forest regressor on a set of stems (e.g., from various patients) may be evaluated by assessing sensitivity, specificity, and area under a receiver-operator characteristic (ROC) curve. For validation, sections annotated by readers as "diseased" may be considered positive, and such sections may be further classified as "true positive" if the random forest predicts percent stenosis >=50% or "false negative" otherwise. Similarly, sections which may be annotated as healthy may be classified as "true negative" if the random forest predicts percent stenosis <$50% and "false positive" otherwise. Sensitivity ($S_e$) and specificity ($S_p$) may be defined as $$S_e=TP/(TP+FN)$$

$$S_p=TN/(TN+FP)$$

An ROC curve may be plotted by evaluating the sensitivity and specificity for different value of cutoffs used to define sections of disease, e.g., $\alpha<=x\ \forall x\in [0\%;\ 100\%]$.

FIG. 3B is an exemplary vascular tree of the machine learning algorithm of FIG. 3A, according to an exemplary embodiment. As previously described, a vascular tree may be split into many stem-crown-root units. FIG. 3B may include an exemplary coronary tree 330. In one embodiment, stems 331 may be defined based on branch points as separators with the corresponding crown and root being the downstream and upstream vasculature respectively. For the exemplary coronary tree 330, epicardial volume, length, diameter, and different ratios may be calculated in the crown 333, root 335, and sibling vessels 337 (if available), and the various ratios may be assigned as features for a given stem 331. In one embodiment, a patient's coronary vasculature may be split into various stem-crown units, where a stem may be comprised of a section of the coronary artery and a crown may be comprised of the downstream vasculature, wherein the power law may relate crown volume and crown length to stem area. This embodiment may indicate the presence or absence of lumen narrowing without specifying where the disease is present, e.g., for a diffuse disease.

FIG. 3C is a block diagram of an exemplary method 350 of improving or further training a machine learning algorithm for generating a lumen narrowing score by validating the trained machine learning algorithm described in FIG. 3A, according to an exemplary embodiment. Validated results from the validation process may provide the basis for an evaluation of lesions with complex morphologies, in addition to providing accurate estimates of percent stenosis of vessel lumen from lumen segmentation(s). The method of FIG. 3C may be performed by server systems 106, based on information, images, and data received from physicians 102 and/or third party providers 104 over electronic network 100.

In one embodiment, step 351 may include identifying a collection of individuals (and their vessel sections), distinct from those used for training the machine learning algorithm (e.g., if FIG. 3A). In one embodiment, step 351 may include identifying individuals who underwent a coronary angiography, where corresponding diseased locations may be identified and quantified using QCA, e.g., by an independent expert at a core laboratory. For example, Coronary QCA data from a subset of the DeFACTO clinical trial (Clinicaltrials.gov\#NCT01233518) may be used as reference ground truth data for the exemplary validation process of method 350 to validate results of exemplary method 300.

In one embodiment, step 353 may include determining a healthy diameter and/or presence of disease for vascular sections of the identified collection of individuals. For example, a set of geometry-based features encompassing the downstream vasculature, upstream vasculature, and a sibling vessel may be used to estimate healthy vessel dimensions of a given section. Step 353 may include partitioning vessel geometry repeatedly into various "stem-crown-root" units and using metrics, e.g., epicardial vascular volume and lumen area which may be known indicators of healthy vessel diameter.

In one embodiment, step 355 may include calculating a correlation coefficient between the predicted and a corresponding measured healthy lumen diameter. The validation process may further include calculating a mean absolute error and a root mean squared error between the predicted and a corresponding measured healthy lumen diameter. The operating point sensitivity and specificity for detecting percent stenosis using the present method may be compared to another method, e.g., a global kernel regression method or an anisotropic kernel regression method. The validation process may further include calculating and/or comparing receiver operator characteristic (ROC) curves for the present method versus other methods (e.g., anisotropic kernel regression and/or global kernel regression).

FIG. 4 is a block diagram of an exemplary method 400 of generating a lumen narrowing score for a particular patient, using a machine learning algorithm (e.g., as described in FIG. 3A), according to an exemplary embodiment. Method 400 may use machine learning to map metrics derived from a particular patient's vasculature to a healthy lumen diameter using a machine learning approach, e.g., a machine learning algorithm trained on a database of healthy vessel sections from a population of individuals, other than the patient. While determining healthy lumen diameter from a patient's own vascular estimations/regressions may be useful for detections of focal lesions, the method 400 is more effective for estimating healthy lumen diameter for non-focal stenoses (e.g., diffuse, ostial, and bifurcation lesions.) The method of FIG. 4 may be performed by server systems 106, based on information, images, and data received from physicians 102 and/or third party providers 104 over electronic network 100.

In one embodiment, step 401 may include receiving a lumen segmentation of the patient's vasculature. The lumen segmentation may include vessel centerlines and/or surface mesh representations of the patient's vasculature.

In one embodiment, step 403 may include splitting the lumen segmentation into stem-crown-root units (e.g., as shown in FIG. 3B), where a stem may include a section of interest for which a healthy diameter may be evaluated, a crown may include vasculature downstream of the section of interest, and a root may include vasculature upstream of the section of interest. Step 403 may also include identifying sibling vessel(s) of the vessel in which the section of interest is located. An exemplary sibling vessel may include a child vessel of the parent vessel, other than the vessel in which the section of interest is located.

In one embodiment, step 405 may include defining and/or extracting features for a vessel segment. For each stem, step 405 may include extracting one or more of the following features for the corresponding crown, root, and sibling vessels (when available), e.g., average, maximum and minimum lumen area (A), volume (V), length (L), V/A, and V/L. Step 405 may also include evaluating local diameter using maximum inscribed spheres and/or evaluating planar area, e.g., the area of lumen along the normal to centerlines. In one embodiment, features that are not available for some stems (e.g., ostial sections may not have a root unit and terminal sections may not have a crown unit) may be assigned a default special value of −1. In one instance, each evaluated segment may represent coronary segmentation between bifurcations.

In one embodiment, step 407 may include comparing features from other parts of the vascular tree to the stem under consideration. For example, step 407 may include using the trained machine learning algorithm (e.g., from FIG. 3A) to analyze one patient vascular stem at a time and use features from the vascular trees of the machine learning algorithm to infer healthy lumen diameter at the stem under consideration.

In one embodiment, step 409 may include inferring a healthy lumen diameter for a vessel segment. For example, an exemplary embodiment may include extracting patient-specific metrics (including the features of step 405), omitting one section at a time, and mapping a database of these metrics to a stored healthy lumen diameter (e.g., from training the machine learning algorithm as described in FIG. 3A). More specifically, the machine learning algorithm may include random forest regression to predict a healthy lumen diameter for the patient. As previously described, random forests may employ an ensemble of decision trees, each of which may be composed of a random subset of features and training data. Each decision tree may map the input feature vector to a continuous variable, and values from the decision trees may be pooled together and averaged to compute a final predictor of healthy lumen diameter ($d_p$).

In one embodiment, step 411 may include determining LNS for a vessel segment. For example, LNS or percent stenosis may be evaluated from the ratio of the local lumen diameter ($d_l$) to the predicted healthy lumen diameter as, $\alpha = (1 - d_p/d_l) \times 100\%$.

In one study, (Sankaran S., Schaap M., Hunley S. C., Min J. K., Taylor C. A., Grady L. (2016) *HALE: Healthy Area of Lumen Estimation for Vessel Stenosis Quantification.* In: Ourselin S., Joskowicz L., Sabuncu M., Unal G., Wells W. (eds) Medical Image Computing and Computer-Assisted Intervention—MICCAI 2016. MICCAI 2016. Lecture Notes in Computer Science, vol 9902. Springer, Cham), method 400 has achieved a correlation coefficient of 0.947 with a mean absolute error of 0.15 mm for predicting lumen diameter of healthy sections. Further, the method may have an operating point sensitivity/specificity of 90%/85% for detecting stenoses. The mean absolute error in percent stenosis on a set of diseased patients may be reduced from 31% in a anisotropic kernel regression to 14% in the present method 300, compared to QCA data.

The general approach of using patient-specific geometric features, including a combination of vascular volume, lumen area, vessel length, and derived features may be used in estimating healthy lumen diameter using a random decision forest regressor. This regressor may be used for vasculatures with different kinds of disease, e.g., acute, diffuse, ostial, and bifurcation. The reference kernel-regression based method described earlier in the present disclosure may be based on local patient-specific data. Such a regression method may capture regions of focal narrowing. Alternate or additional regression methods may account for population data and capture other disease morphologies. Yet another method, e.g., a method for detection of diffuse lesions, may include a population-based machine learning approach, where the output metric (LNS) may provide indications of the presence or absence of diffuse lesions.

The present systems and methods may be used with any lumen segmentation algorithm. Depending on the application, the present systems and methods may be used, for example, with an automated lumen segmentation algorithm for on-site evaluation of percent stenosis, or be used with a semi-automated method offline or in a core-lab setting. The present system and methods may provide an accurate QCT assessment tool that may involve the coupling of an accurate lumen segmentation algorithm with an accurate algorithm for evaluation of percent stenosis. Such an assessment tool may perform well against QCA, and better than an anisotropic kernel regression for the same lumen segmentation.

One further embodiment may include restricting features from being calculated on sections that may be diseased. For example, such an embodiment may include an iterative algorithm where a section, once identified as diseased while training the machine learning algorithm, may be not used in the estimation of features for other sections. Embodiments may also include higher order metrics, e.g., area gradients.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of identifying a lumen diameter of a patient's vasculature, the method comprising:
   receiving a data set including one or more lumen segmentations of known healthy vessel segments of a plurality of individuals;
   extracting, for each known healthy vessel segment, a lumen feature for a section of vasculature upstream of the healthy vessel segment;
   extracting, for each known healthy vessel segment, a lumen feature for a section of vasculature downstream of the healthy vessel segment; and
   computing a population-based healthy lumen diameter based on the extracted lumen feature for the section of vasculature upstream of the healthy vessel segment and based on the extracted lumen feature for the section of vasculature downstream of the healthy vessel segment.

2. The method of claim 1, further comprising:
   computing a patient-specific healthy lumen diameter based on the population-based healthy lumen diameter.

3. The method of claim 2, further comprising:
   computing a patient-specific lumen narrowing score based on the patient-specific healthy lumen diameter.

4. The method of claim 1, further comprising:
   receiving a lumen segmentation of a patient's vasculature;
   determining a section of the patient's vasculature; and
   determining a patient-specific healthy lumen diameter of the section of the patient's vasculature using the determined population-based healthy lumen diameter.

5. The method of claim 4, further comprising:
   splitting each of the lumen segmentations of the known healthy vessel segments into sub-units, where one unit of the sub-units corresponds to the determined section of the patient's vasculature.

6. The method of claim 1, further comprising:
   generating an estimate of fractional flow reserve, generating an estimate or sensitivity of a fractional flow reserve estimate, or generating a model based on the patient-specific lumen narrowing score.

7. The method of claim 1, further comprising:
   generating an estimate of fractional flow reserve, generating an estimate or sensitivity of a fractional flow reserve estimate, or generating a model based on the patient-specific healthy lumen diameter.

8. The method of claim 1, wherein the one or more lumen features include average maximum and minimum lumen area, volume, and length.

9. A system for identifying a lumen diameter of a patient's vasculature, the system comprising:
   a processor configured to perform a method including:
      receiving a data set including one or more lumen segmentations of known healthy vessel segments of a plurality of individuals;
      extracting, for each known healthy vessel segment, a lumen feature for a section of vasculature upstream of the healthy vessel segment;
      extracting, for each known healthy vessel segment, a lumen feature for a section of vasculature downstream of the healthy vessel segment; and
      computing a population-based healthy lumen diameter based on the extracted lumen feature for the section of vasculature upstream of the healthy vessel segment and based on the extracted lumen feature for the section of vasculature downstream of the healthy vessel segment.

10. The system of claim 9, wherein the system is further configured for:
computing a patient-specific healthy lumen diameter based on the population-based healthy lumen diameter.

11. The system of claim 9,
computing a patient-specific lumen narrowing score based on the patient-specific healthy lumen diameter.

12. The system of claim 9, wherein the system is further configured for:
receiving a lumen segmentation of a patient's vasculature;
determining a section of the patient's vasculature; and
determining a patient-specific healthy lumen diameter of the section of the patient's vasculature using the determined population-based healthy lumen diameter.

13. The system of claim 12, wherein the system is further configured for:
splitting each of the lumen segmentations of the known healthy vessel segments into sub-units, where one unit of the sub-units corresponds to the determined section of the patient's vasculature.

14. The system of claim 12, wherein the system is further configured for:
generating an estimate of fractional flow reserve, generating an estimate or sensitivity of a fractional flow reserve estimate, or generating a model based on the patient-specific lumen narrowing score.

15. The system of claim 9, wherein the system is further configured for:
generating an estimate of fractional flow reserve, generating an estimate or sensitivity of a fractional flow reserve estimate, or generating a model based on the patient-specific healthy lumen diameter.

16. The system of claim 9, wherein the one or more lumen features include average maximum and minimum lumen area, volume, and length.

17. A non-transitory computer readable medium for use on a computer system containing computer-executable programming instructions for performing a method of identifying a lumen diameter of a patient's vasculature, the method comprising:
receiving a data set including one or more lumen segmentations of known healthy vessel segments of a plurality of individuals;
extracting, for each known healthy vessel segment, a lumen feature for a section of vasculature upstream of the healthy vessel segment;
extracting, for each known healthy vessel segment, a lumen feature for a section of vasculature downstream of the healthy vessel segment; and
computing a population-based healthy lumen diameter based on the extracted lumen feature for the section of vasculature upstream of the healthy vessel segment and based on the extracted lumen feature for the section of vasculature downstream of the healthy vessel segment.

18. The non-transitory computer readable medium of claim 17, the method further comprising:
computing a patient-specific healthy lumen diameter based on the population-based healthy lumen diameter.

19. The non-transitory computer readable medium of claim 17, the method further comprising:
computing a patient-specific lumen narrowing score based on the patient-specific healthy lumen diameter.

20. The non-transitory computer readable medium of claim 17, the method further comprising:
receiving a lumen segmentation of a patient's vasculature;
determining a section of the patient's vasculature; and
determining a patient-specific healthy lumen diameter of the section of the patient's vasculature using the determined population-based healthy lumen diameter.

* * * * *